United States Patent
Sciavolino et al.

(10) Patent No.: US 9,242,008 B2
(45) Date of Patent: Jan. 26, 2016

(54) MINERAL AMINO-ACID COMPLEXES OF FATTY ACIDS

(71) Applicant: Thetis Pharmaceuticals LLC, Southport, CT (US)

(72) Inventors: Frank C. Sciavolino, Waterford, CT (US); Gary Mathias, Ridgefield, CT (US)

(73) Assignee: Thetis Pharmaceuticals LLC, Southport, CT (US)

(*) Notice: Subject to any disclaimer, the term of this patent is extended or adjusted under 35 U.S.C. 154(b) by 0 days.

(21) Appl. No.: 14/504,247

(22) Filed: Oct. 1, 2014

(65) Prior Publication Data

US 2015/0366980 A1  Dec. 24, 2015

Related U.S. Application Data

(60) Provisional application No. 62/013,904, filed on Jun. 18, 2014.

(51) Int. Cl.
*A61K 31/42* (2006.01)
*A61K 47/48* (2006.01)
*A61K 31/202* (2006.01)
*A61K 45/06* (2006.01)

(52) U.S. Cl.
CPC ......... *A61K 47/48076* (2013.01); *A61K 31/202* (2013.01); *A61K 45/06* (2013.01)

(58) Field of Classification Search
USPC ........................................................ 514/374
See application file for complete search history.

(56) References Cited

U.S. PATENT DOCUMENTS

| | | | |
|---|---|---|---|
| 4,599,152 A | 7/1986 | Ashmead | |
| 5,795,909 A | 8/1998 | Shashoua et al. | |
| 6,372,790 B1 | 4/2002 | Bonhomme et al. | |
| 6,491,950 B1 | 12/2002 | Gutierrez-Rocca et al. | |
| 6,517,870 B1 | 2/2003 | Nishii et al. | |
| 6,602,902 B2 | 8/2003 | Shashoua et al. | |
| 6,667,064 B2 | 12/2003 | Surette | |
| 6,720,001 B2 | 4/2004 | Chen et al. | |
| 6,881,854 B2 | 4/2005 | Ptock et al. | |
| 6,893,627 B2 | 5/2005 | Ribnicky et al. | |
| 7,105,572 B2 | 9/2006 | Sato | |
| 7,195,914 B2 | 3/2007 | Surette | |
| 7,199,151 B2 | 4/2007 | Shashoua et al. | |
| 7,214,387 B2 | 5/2007 | Sanghvi et al. | |
| 7,223,770 B2 | 5/2007 | Zhang et al. | |
| 7,304,089 B2 | 12/2007 | Kramer et al. | |
| 7,429,395 B2 | 9/2008 | Campbell-Tofte | |
| 7,553,870 B2 | 6/2009 | Shibuya | |
| 7,579,025 B2 | 8/2009 | Campbell-Tofte | |
| 7,619,002 B2 | 11/2009 | Shibuya | |
| 7,666,898 B2 | 2/2010 | Chang et al. | |
| 7,670,612 B2 | 3/2010 | Miller | |
| 7,973,073 B2 | 7/2011 | Mylari et al. | |
| 8,034,842 B2 | 10/2011 | Bryhn et al. | |
| 8,058,312 B2 | 11/2011 | Kim et al. | |
| 8,076,377 B2 | 12/2011 | Kim et al. | |
| 8,178,707 B2 | 5/2012 | Gleason et al. | |
| 8,378,131 B2 | 2/2013 | Gleason et al. | |
| 8,710,041 B2 | 4/2014 | Osterloh et al. | |
| 8,765,811 B2 | 7/2014 | Mylari et al. | |
| 8,906,964 B2 | 12/2014 | Bobotas et al. | |
| 8,933,124 B2 * | 1/2015 | Mylari et al. | 514/554 |
| 9,012,501 B2 | 4/2015 | Sachetto et al. | |
| 2003/0077335 A1 | 4/2003 | Richardson et al. | |
| 2003/0220301 A1 | 11/2003 | Lal et al. | |
| 2005/0158374 A1 | 7/2005 | Wong et al. | |
| 2005/0165102 A1 | 7/2005 | Wong et al. | |
| 2005/0182029 A1 | 8/2005 | Lal | |
| 2005/0182089 A1 | 8/2005 | Friedl et al. | |
| 2006/0159746 A1 | 7/2006 | Troup et al. | |
| 2006/0229359 A1 | 10/2006 | Zhang et al. | |
| 2006/0240095 A1 | 10/2006 | Junien et al. | |
| 2007/0060532 A1 | 3/2007 | Junien et al. | |
| 2007/0207196 A1 | 9/2007 | Zhang | |
| 2008/0045559 A1 | 2/2008 | Zhang et al. | |
| 2008/0200533 A1 | 8/2008 | Krishnan | |
| 2008/0260819 A1 | 10/2008 | Fleming et al. | |
| 2009/0047340 A1 | 2/2009 | Guilford | |
| 2009/0054513 A1 | 2/2009 | Webster et al. | |
| 2009/0156612 A1 | 6/2009 | Kuroita et al. | |
| 2009/0227560 A1 | 9/2009 | Kuroita et al. | |
| 2010/0035990 A1 | 2/2010 | Bryhn et al. | |
| 2010/0105773 A1 | 4/2010 | Smith et al. | |
| 2010/0121048 A1 | 5/2010 | Kuroita et al. | |

(Continued)

FOREIGN PATENT DOCUMENTS

| | | |
|---|---|---|
| AU | 2012227298 A1 | 4/2014 |
| EP | 2705844 A1 | 3/2014 |

(Continued)

OTHER PUBLICATIONS

"Amino Acid Structures." Web. Nov. 14, 2013. http://www.cem.msu.edu/-cem252/sp97/ch24/ch24aa/html.
"Cold Spring Harbor Protocols." 2006. Web. Nov. 13, 2013. http://cshprotocols.cship.org.
"Eicosapentaenoic Acid pKa." STN Registry File. Web. Nov. 14, 2013.
"Prandimet." RxList. Web. Nov. 14, 2013. http://www.rxlist.com/prandimet-drug.htm.
Charles et al. "Treatment with Metformin of Non-Diabetic Men with Hypertension, Hypertriglyceridaemia and Central Fat Distribution: The BIGPRO 1.2 Trial." *Diabetes Metab. Res. Rev.* 16(2000):2-7.
Goldberg et al. "Lifestyle and Metformin Treatment Favorably Influence Lipoprotein Subfraction Distribution in the Diabetes Prevention Program." *J. Clin. Endocrinol. Metab.* pub. ahead of print Aug. 26, 2013.

(Continued)

*Primary Examiner* — Rei-Tsang Shiao
(74) *Attorney, Agent, or Firm* — Mintz Levin Cohn Ferris Glovsky and Popeo, P.C.; Muriel Liberto, Esq.

(57) ABSTRACT

The present invention relates to compound of Formula III comprising an amino acid component, a divalent metal component, and a counter-ion component, compositions containing same, and methods of use.

27 Claims, 1 Drawing Sheet

(56) References Cited

U.S. PATENT DOCUMENTS

| | | |
|---|---|---|
| 2010/0137587 A1 | 6/2010 | Takanobu et al. |
| 2010/0324010 A1 | 12/2010 | Imaeda et al. |
| 2011/0046053 A1 | 2/2011 | Kidron |
| 2011/0052678 A1 | 3/2011 | Shantha et al. |
| 2011/0171142 A1 | 7/2011 | Lara |
| 2011/0237813 A1 | 9/2011 | Gleason et al. |
| 2012/0178813 A1 | 7/2012 | Mylari et al. |
| 2013/0095140 A1 | 4/2013 | Baron et al. |
| 2013/0281535 A1 | 10/2013 | Mylari et al. |
| 2013/0281536 A1 | 10/2013 | Pinchera et al. |
| 2014/0100273 A1 | 4/2014 | Bobotas et al. |
| 2014/0107360 A1 | 4/2014 | Mylari et al. |
| 2014/0118419 A1 | 5/2014 | Wu et al. |
| 2014/0249221 A1 | 9/2014 | Mylari et al. |

FOREIGN PATENT DOCUMENTS

| | | |
|---|---|---|
| WO | WO-03068209 A1 | 8/2003 |
| WO | WO-03/093449 A2 | 11/2003 |
| WO | WO-2004/028469 A2 | 4/2004 |
| WO | WO-2004082402 A2 | 9/2004 |
| WO | WO-2005041923 A1 | 5/2005 |
| WO | WO-2005042539 A1 | 5/2005 |
| WO | WO-2005118612 A1 | 12/2005 |
| WO | WO-2009038396 A2 | 3/2009 |
| WO | WO-2010/012799 A2 | 2/2010 |
| WO | WO-2010127099 A2 | 11/2010 |
| WO | WO-2013103902 A1 | 7/2013 |
| WO | WO-2014/011895 A2 | 1/2014 |

OTHER PUBLICATIONS

Sugiyama et al. "Eicosapentaenoic Acid Lowers Plasma and Liver Cholesterol Levels in the Presence of Peroxisome Profferators-Activate Receptor Alpha." *Life Sciences*. 83(2008):19-28.

Wulffele et al. "The Effect of Metformin on Blood Pressure, Plasma Cholesterol and Triglycerides in Type 2 Diabetes Mellitus: A Systematic Review." *J. Intern. Med.* 256.1(2004):1-14.

International Search Report issued in PCT/US2013/049984 on Nov. 28, 2013.

* cited by examiner

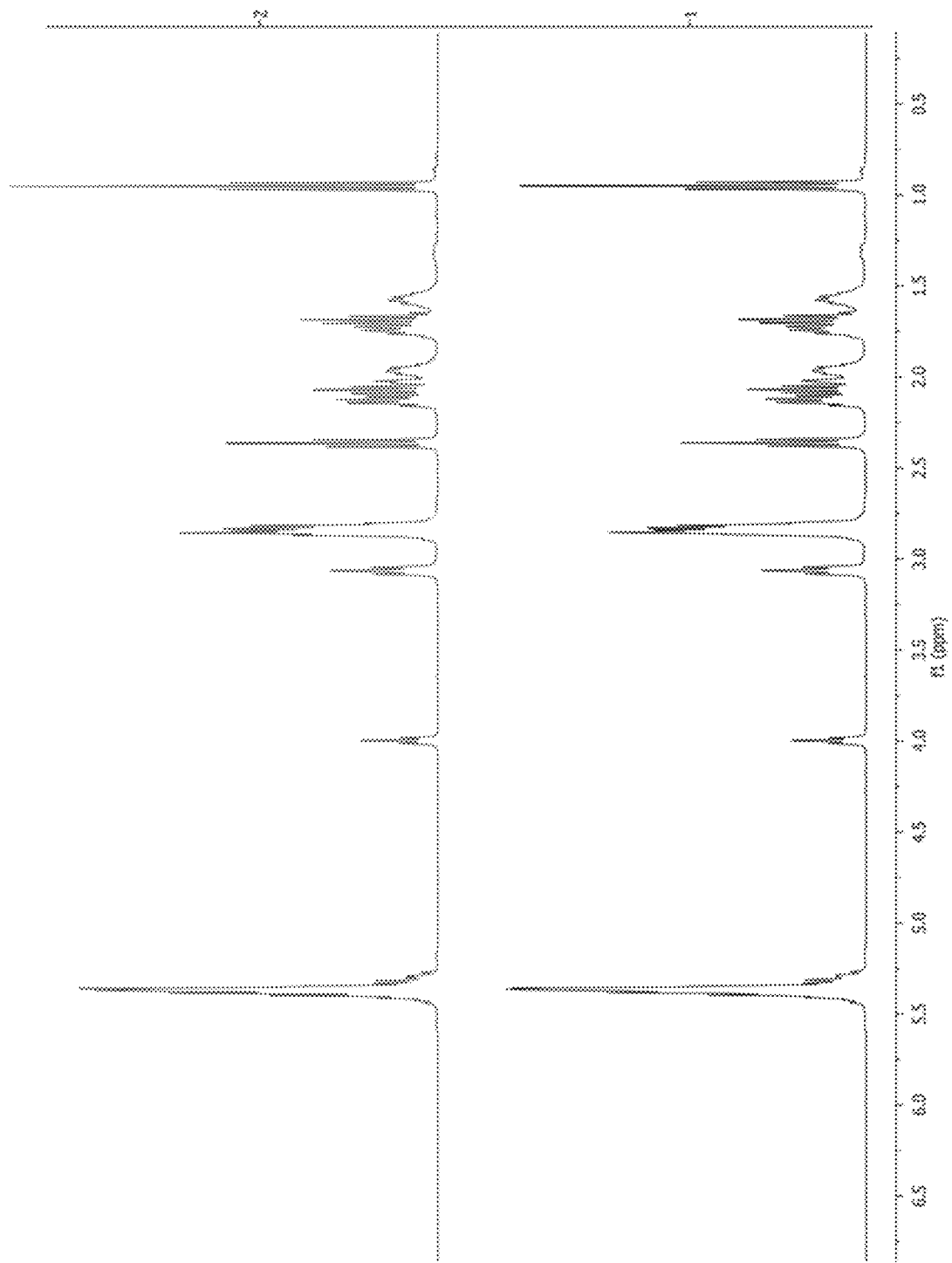

MINERAL AMINO-ACID COMPLEXES OF FATTY ACIDS

FIELD OF THE INVENTION

The present invention relates to the field of drug delivery and particularly the use of mineral amino acid complexes of fatty acids for delivery of the fatty acids to a subject.

BACKGROUND

Amino acid chelates for delivery of minerals to biological tissues are described in U.S. Pat. No. 4,863,898. Amino acid chelates in this context refers to the product resulting from the reaction of a polypeptide, dipeptide or naturally occurring alpha amino acid with a metal ion having a valence of two or more to form a ring structure in which the positive electrical charges of the metal ion are neutralized by the electrons available through the carboxylate or free amino groups of the alpha amino acid. As described by U.S. Pat. No. 4,863,898, chelate formation through neutralization of the positive charges of the divalent metal ions can be through the formation of ionic, covalent or coordinate covalent bonding. U.S. Pat. No. 4,863,898 states that it provides an advantage over the prior art metal chelates, which are effective to increase metal content in biological tissues generally, by providing metal chelates targeted to specific tissues. Manganese, calcium, iron, magnesium, copper, and zinc amino acid chelates are among those described.

Polyunsaturated fatty acids of the omega-3 series ("omega-3 fatty acids") have shown a wide spectrum of biological activities suggesting their possible usefulness in treating a range of diseases and disorders including metabolic disorders, cardiovascular complications, inflammatory diseases, central nervous system disorders, and ophthalmic complications. But the poor aqueous solubility of omega-3 fatty acids limits their utility as therapeutic agents and as nutraceutical additives to food and drink due to a phenomenon referred to as solubility-limited absorption which limits the plasma levels that can be achieved following oral administration. In fact, the omega-3 fatty acids are essentially insoluble in water and both the free acid and sodium salt forms create soap-like emulsions when mixed with water. Thus, although omega-3 fatty acids are absorbed following oral administration, the relatively low plasma levels achieved cannot be increased simply by increasing the dose administered.

WO 2014/011895 describes fatty acid salts of eicosapentaenoic acid (EPA) with lysine or docosahexaenoic acid (DHA) or EPA with metformin, piperazine, and meglumine.

In addition to their poor aqueous solubility, omega-3 fatty acids suffer from susceptibility to lipid oxidation. This oxidation leads to formation of undesirable fishy and rancid off-flavors that render compositions comprising them less palatable.

There is a need to develop compositions able to deliver omega-3 fatty acids at much higher plasma levels than is possible using the currently available free fatty acid, sodium salt, or ester forms, in order to fulfill the therapeutic promise of these compounds and translate the many promising in vitro and cellular pharmacology observations into clinical benefits. Such compositions should demonstrate increased aqueous solubility of omega-3 fatty acids which would facilitate their use in both oral dosage forms, ophthalmic drops, and intravenous dosage forms. There is also a need to develop compositions that provide improved stability of the omega-3 fatty acids against lipid oxidation. The present invention addresses these needs.

SUMMARY OF THE INVENTION

The present invention provides mineral amino acid complexes of fatty acids which possess superior chemical and physical stability compared to the free fatty acid, ethyl ester, or glyceryl ester forms of the fatty acids. In addition, the present compounds display increased bioavailability of the fatty acid component compared to the free fatty acid or ester forms of the fatty acids.

In particular, the present invention provides a compound of Formula III comprising a peptide component, which consists of two amino acids coordinated around a metal component, a metal component, and a counter-ion component,

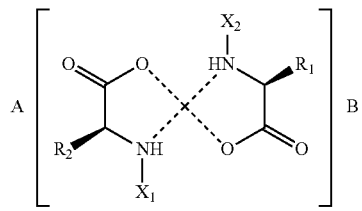

wherein $R_1$ and $R_2$ each refer to a side chain of an amino acid coordinated around X;

$X_1$ and $X_2$ are independently selected from H and —CO—Z, where Z is a peptide moiety incorporating from 1 to 5 amino acids, or a pharmaceutically acceptable salts thereof;

X is selected from magnesium ($Mg^{2+}$), calcium ($Ca^{2+}$), or Zinc ($Zn^{2+}$) as the metal component; and A and B are each an omega-3 fatty acid which serve as the counter-ion component. A and B may be the same or different and B may be present or absent. In one embodiment, the omega-3 fatty acid is independently selected from eicosapentaenoic acid (EPA), docosahexaenoic acid (DHA), and docosapentaenoic acid (DPA). In one embodiment, the counter-ion component comprises two omega-3 fatty acids.

In one embodiment, $R_1$ and $R_2$ are the same and both are lysine side chains or arginine side chains.

In one embodiment, $R_1$ and $R_2$ are the same and both are lysine side chains or arginine side chains and $X_1$ and $X_2$ are the same and are hydrogen (H).

The present invention also provides a composition comprising one or more compounds of Formula III, and a carrier. The composition may be a pharmaceutical or nutriceutical composition and the carrier is acceptable for administration to humans.

In one embodiment, the composition is a nutriceutical composition in the form of a food or drink product.

In one embodiment, the composition is a pharmaceutical composition and comprises an amount of the compound effective to lower elevated serum triglycerides in a subject, preferably a human subject. In one embodiment, the subject is a human subject having severe hypertriglyceridemia. In one embodiment, the subject is a human subject having non-severe hypertriglyceridemia.

In one embodiment, the composition is a pharmaceutical composition and comprises an amount of the compound effective to treat a metabolic disorder selected from the group consisting of abnormal glucose metabolism manifesting in diabetes or pre-diabetes, abnormal lipid metabolism manifesting as hypertriglyceridemia, i.e., elevated triglycerides, mixed dyslipidemia, fatty liver, and combined abnormal glucose and lipid metabolism manifesting in obesity. In one embodiment, a composition of the invention is used in a method for treating a disease or disorder selected from diabetes, pre-diabetes, hypertriglyceridemia, dyslipidemia, fatty liver, and obesity.

In one embodiment, the composition is a pharmaceutical composition and comprises an amount of the compound effective to treat a disease or disorder selected from the group consisting of arthritis, irritable bowel syndrome, atrial fibrillation, ophthalmic inflammation disorders, dry eye syndrome, traumatic brain injury, familial adenomatous polyposis, sporadic adenomatous polyposis, epilepsy, epileptic syndrome, Alzheimer's disease, and attention deficit hyperactivity disorder (ADHD).

In one embodiment, the composition is a pharmaceutical composition and comprises an amount of the compound effective to treat or manage pain in a subject. In one embodiment, the pain is neuropathic pain or nociceptive pain.

The present invention also provides a package or kit comprising a unit dosage form of a composition described herein, at least one container for holding the unit dosage forms, and instructions for use.

The present invention also provides for the use of a composition described herein for treating a disease or disorder in a subject, preferably a human subject, the disease or disorder selected from the group consisting of hypertriglyceridemia, severe hypertriglyceridemia, pre-diabetes, fatty liver disease, obesity, arthritis, irritable bowel syndrome, atrial fibrillation, ophthalmic inflammation disorders, dry eye syndrome, and traumatic brain injury.

The present invention also provides a method of treating a disease or disorder in a subject, preferably a human subject, the method comprising administering to the subject an amount of a composition described herein effective to treat the disease or disorder in the subject, the disease or disorder selected from the group consisting of hypertriglyceridemia, severe hypertriglyceridemia, pre-diabetes, fatty liver disease, obesity, arthritis, irritable bowel syndrome, atrial fibrillation, ophthalmic inflammation disorders, dry eye syndrome, and traumatic brain injury.

BRIEF DESCRIPTION OF THE FIGURES

FIG. 1: Proton NMR spectrum of magnesium bis-lysinate bis-EPA taken on the day the compound was synthesized (upper trace) and 60-days later (lower trace) with the compound having been exposed to air at room temperature for the entire 60-day period.

DETAILED DESCRIPTION OF THE INVENTION

The invention relates to complexes of amino acids and divalent metals in which the amino acids are coordinated around a metal component and the metal coordinated amino acids are ionically bound to a counterion component. Thus, the compounds described here consist of (i) a metal component; (ii) an amino acid component which consists of two amino acids coordinated around the metal component; and (iii) a counterion component. The counterion component may consist of one or two counterions, designated A and B respectively. A and B may be the same or different and B may be present or absent.

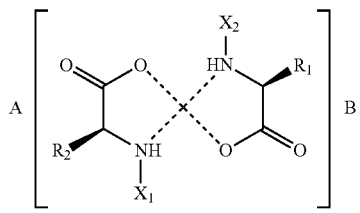

Formula III

The divalent metal component is selected from magnesium ($Mg^{2+}$), calcium ($Ca^{2+}$), or zinc ($Zn^{2+}$). The counterion component comprises at least one counterion contributed by an anion of a polyunsaturated fatty acid of the omega-3 series. In the context of the present disclosure, a polyunsaturated fatty acid of the omega-3 series may also be referred to interchangeably as a "PUFA" or an "omega-3 fatty acid". Each of these terms refers to long-chain polyunsaturated fatty acids having 16 to 24 carbon atoms ($C_{16}$-$C_{24}$). In one aspect, the compounds of the invention comprise a counterion component comprising or consisting of one or two omega-3 fatty acids, preferably those having 20 to 22 carbon atoms ($C_{20}$-$C_{22}$), such as eicosapentaenoic acid (EPA), docosahexaenoic acid (DHA), and docosapentaenoic acid (DPA). Also provided are compositions comprising the compounds described herein and methods of making and using same.

The compounds of the invention provide for the systemic delivery of the ionically bound omega-3 fatty acid when administered to a subject. The compounds of the invention advantageously provide higher bioavailability of the omega-3 fatty acid component compared with a standard dosage form of the fatty acid. Thus, the compounds of the invention are useful for the efficient delivery of therapeutically effective amounts of omega-3 fatty acids to a subject.

In the context of any of the methods of the present invention, the subject may be a human or a non-human mammal. The non-human mammal may be, for example, a non-human primate, a dog, cat, a rodent (e.g., a mouse, a rat, a rabbit), a horse, a cow, a sheep, a goat, a chicken, or any other non-human mammal.

The compounds of the invention may be mono- or bis-salts of the omega-3 fatty acids with the metal-coordinated amino acid component. Preferably, the counter ion component comprises or consists of one or two omega-3 fatty acid anions independently selected from eicosapentaenoic acid (EPA) anion, docosahexaenoic acid (DHA) anion, and docosapentaenoic acid (DPA) anion.

In one embodiment, the compounds of the invention are di-lysinate salts in which each amino acid coordinated around the divalent metal consists of the amino acid lysine. In one embodiment, a compound of the invention comprises a metal-amino acid component selected from magnesium di-lysinate, calcium di-lysinate, or zinc di-lysinate.

The compounds of the invention are useful for treating diseases and disorders responsive to omega-3 fatty acids. Thus, the invention provides pharmaceutical compositions comprising one or more of the compounds of the invention. The pharmaceutical compositions of the invention can be used as monotherapy or adjunctive therapy. The pharmaceutical compositions of the invention can be administered alone or in combination with one or more additional therapeutic agents or therapies, for example as part of a therapeutic regimen that includes, e.g., aspects of diet and exercise.

In one embodiment, a pharmaceutical composition of the invention is used in the treatment of dyslipidemic disorders such as hypertriglyceridemia and mixed dyslipidemias, type 2 diabetes, and insulin resistance, as well as in the treatment of familial adenomatous polyposis (FAP) and sporadic adenomatous polyposis. In another embodiment, a pharmaceutical composition of the invention is used in treating atopic dermatitis.

Compositions comprising the compounds of the invention can also be formulated as nutritional additives or supplements. Such compositions may be used as a dietary supplement or food ingredient, either for human or non-human consumption. Accordingly, the invention also provides food products and ingredients (e.g., additives or supplements), for human and/or non-human consumption comprising one or more compounds of the invention.

In one embodiment, at least one compound of the invention is formulated as a pharmaceutical or nutriceutical composition along with a suitable carrier. The carrier may be suitable for administration to humans or animals, or both.

In one embodiment, the composition is a nutriceutical composition, including an additive or supplement. In one embodiment, the invention provides a food or drink product comprising a nutriceutical composition of the invention.

In one embodiment, the composition is a pharmaceutical composition and comprises an amount of the compound effective to treat dyslipidemic disorders such as hypertriglyceridemia and mixed dyslipidemias, type 2 diabetes, and insulin resistance. In one embodiment, the pharmaceutical composition comprises an amount of a compound of Formula III (or mixture of compounds of Formula III) effective to lower elevated serum triglycerides in a subject, preferably a human subject. In one embodiment, the amount is effective to lower elevated serum triglycerides in a human subject by at least 0.5 mmol/L, preferably by at least 1 mmol/L. In one embodiment, the subject is a human subject having severe hypertriglyceridemia characterized by serum triglyceride levels of from 500 to 2,000 mg/dl.

In one embodiment, the composition is a pharmaceutical composition and comprises an amount of a compound of Formula III (or mixture of compounds of Formula III) effective to treat insulin resistance, pre-diabetes, fatty liver disease, or obesity in a subject, preferably a human subject.

In one embodiment, the composition is a pharmaceutical composition and comprises an amount of a compound of Formula III (or mixture of compounds of Formula III) effective to treat a disease or disorder selected from the group consisting of arthritis, irritable bowel syndrome, atrial fibrillation, ophthalmic inflammation disorders, dry eye syndrome, traumatic brain injury, and familial adenomatous polyposis.

The invention also provides a package or kit comprising a unit dosage form of a composition of the invention, at least one container for holding the unit dosage form, and instructions for use.

The invention also provides a method of treating a disease or disorder in a subject, preferably a human subject, the method comprising administering to the subject an amount of a compound of Formula III (or mixture of compounds of Formula III) effective to treat the disease or disorder in the subject, the disease or disorder selected from the group consisting of hypertriglyceridemia, severe hypertriglyceridemia, insulin resistance, pre-diabetes, fatty liver disease, obesity, arthritis, irritable bowel syndrome, atrial fibrillation, ophthalmic inflammation disorders, dry eye syndrome, traumatic brain injury, epilepsy, or epileptic syndrome. The invention also provides method of treating or managing pain in a subject by administering to the subject an amount of a compound of Formula III (or mixture of compounds of Formula III) effective to ameliorate or manage the pain.

Properties

The compounds of the invention are sparingly soluble or nearly insoluble in water at physiological pH and are also insoluble in most organic solvents. However, they are soluble in aqueous acidic media where the pH is about 5.5 or less. The low aqueous solubility of the compounds provides superior physical and chemical stability. For example, the compounds of Formula III are solids and are very stable against oxidative degradation of the omega-3 fatty acid component, particularly when compared to the free fatty acid or fatty acid ester forms of the fatty acids, which are highly susceptible to oxidative degradation in their liquid forms AND consequently tend to degrade when exposed to air or humidity. In contrast, the compounds described here are, for example, stable to air, oxygen, and humidity such that no change in physical properties, such as flow characteristics, or in chemical properties, as measured by NMR spectroscopy, occur following days of storage in an open vial at room temperature and standard humidity.

In addition, the compounds of the invention also provide unexpectedly high bioavailability of the fatty acid component due to the tendency of the ionic complex to completely dissociate at acidic pH within the range of the pH that occurs in the stomach. Accordingly, the present invention provides compounds that combine the advantageous properties of high chemical and physical stability with high bioavailability of the fatty acid component.

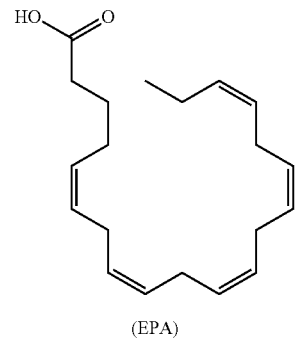

Formula I (EPA)

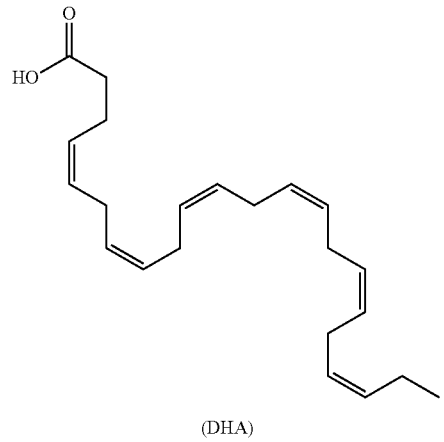

Formula II (DHA)

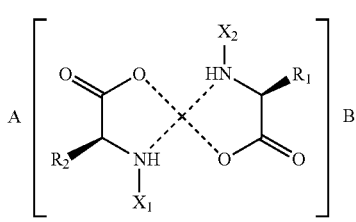

Formula III

The present invention relates to compounds of Formula III comprising an amino acid component, which consists of two amino acids coordinated around a divalent metal X, a metal component X, and a counter-ion component consisting of A and B, where A and B are the same or different and B is either present or absent, A and B being independently selected from eicosapentaenoic acid anion (EPA anion, formula IV), docosahexaenoic acid anion (DHA anion, formula V), and docosapentaenoic acid anion (DPA). The amino acids of the amino acid component each comprise a side chain, $R_1$ and $R_2$ respectively. The metal component X is a divalent metal selected from $Mg^{2+}$, $Ca^{2+}$, or $Zn^{2+}$. $X_1$ and $X_2$ are independently selected from H and —CO—Z, where Z is a polypeptide moiety incorporating from 1 to 5 amino acids, or a pharmaceutically acceptable salts thereof.

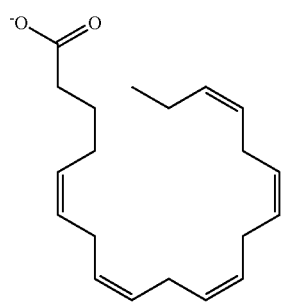

(EPA anion)

Formula IV

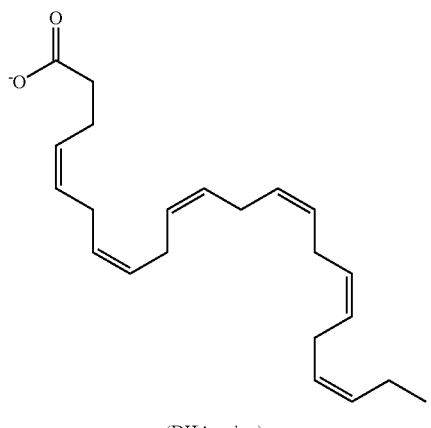

(DHA anion)

Formula V

In one embodiment, $R_1$ and $R_2$ are the same and consist of lysine or arginine side chains. In one embodiment, the two amino acids coordinated around the metal component are selected from lysine and arginine and $X_1$ and $X_2$ are H.

In one embodiment, a composition of the invention comprises one or more of a compound of Formula III selected from the group consisting of calcium bis-lysinate bis-EPA monohydrate (formula VI), calcium bis-lysinate mono-EPA (formula VII), calcium bis-lysinate bis-DHA (formula VIII), magnesium bis-lysinate bis-EPA dihydrate (formula IX), magnesium bis-lysinate mono-EPA (formula X), magnesium bis-lysinate bis-DHA dihydrate (formula XI), and zinc bis-lysinate bis-EPA monohydrate (formula XII).

In certain embodiments, the invention provides a solvate of a salt described herein. A "solvate" refers to a form of salt bound by a non-covalent bond to another molecule (such as a polar solvent). Such solvates are typically crystalline solids having a substantially fixed molar ratio of solute and solvent. When the solvent is water, the solvate formed is a hydrate. Example hydrates include hemihydrates, mono hydrates, dihydrates, etc.

In one embodiment, the invention provides a crystalline form of a salt described herein. In one embodiment, the invention provides a polymorph of an ionic salt described herein.

Compositions

The following describes compositions comprising the compounds of the invention formulated as a pharmaceutical composition or as a nutraceutical additive or supplement. The compounds of the invention may be formulated alone or together with one or more additional compounds, active pharmaceutical agents (API), nutritional agents, or therapeutic agents in the same dosage form. In one embodiment, a composition of the invention comprises or consists of a physical mixture of two or more of the compounds of Formula III in the same dosage form, along with any suitable excipients or carriers.

In one embodiment, the composition comprises a physical mixture of two compounds of Formula III in a single solid dosage form, preferably an oral dosage form. In one aspect of this embodiment, A and B are the same in each compound but different between the two compounds. For example, the first compound of Formula III in the composition may contain bis-EPA (A and B are both EPA), bis-DHA, or bis-DPA and the second compound of Formula III in the composition may contain any of the foregoing, provided it is different from the fatty acid component of the first compound. In a further aspect, one or both of the first and second compounds of Formula III in the composition contains a different omega-3 fatty acid at A and B. For example, one or both of the first and second compounds of Formula III may contain bis-EPA/DHA, bis-EPA/DPA, or bis-DHA/DPA, provided the fatty acid component of the first compound is different from that of the second. In one aspect of this embodiment, the two compounds of Formula III are present in the composition in a defined weight ratio. In a further aspect the defined ratio is from 1.25:1 to 4:1, or a ratio of 2:1, 3:1, or 5:4.

In one embodiment, the two compounds of Formula III present in the composition are selected from the following:
calcium bis-lysinate bis-EPA and calcium bis-lysinate bis-DHA,
magnesium bis-lysinate bis-EPA and magnesium bis-lysinate bis-DHA,
magnesium bis-lysinate bis-EPA and magnesium bis-lysinate mono-EPA mono-DHA (also referred to as magnesium bis-lysinate bis EPA/DHA),
zinc bis-lysinate bis-EPA and zinc bis-lysinate bis-DHA,
calcium bis-arginate bis-EPA and calcium bis-arginate bis-DHA,
magnesium bis-arginate bis-EPA and magnesium bis-arginate bis-DHA,
zinc bis-arginate bis-EPA and zinc bis-arginate bis-DHA,
calcium bis-lysinate bis-EPA and calcium bis-lysinate bis-DPA, magnesium bis-lysinate bis-EPA and magnesium bis-lysinate bis-DPA,
zinc bis-lysinate bis-EPA and zinc bis-lysinate bis-DPA,
calcium bis-lysinate bis-DHA and calcium bis-lysinate bis-DPA,
magnesium bis-lysinate bis-DHA and magnesium bis-lysinate bis-DPA,
zinc bis-lysinate bis-DHA and zinc bis-lysinate bis-DPA, and
calcium bis-lysinate bis-EPA and calcium bis-lysinate mono-EPA mono-DHA (also referred to as calcium bis-lysinate bis EPA/DHA).

In one embodiment, the two compounds of Formula III present in the composition are selected from (i) calcium bis-lysinate bis-EPA and calcium bis-lysinate bis-DHA, (ii) magnesium bis-lysinate bis-EPA and magnesium bis-lysinate bis-DHA, and (iii) zinc bis-lysinate bis-EPA and zinc bis-lysinate bis-DHA.

In one embodiment, the composition comprises or consists of a physical mixture of one, two or more of the compounds of the invention along with another API, nutritional agent, or therapeutic agent in the same dosage form, along with any suitable excipients or carriers. In one embodiment, the composition comprises a physical mixture of two compounds of Formula III in a ratio of from 1.25:1 to 4:1, or a ratio of 2:1, 3:1, or 5:4, along with an additional API, therapeutic agent, or nutraceutical agent in a single dosage form. In one aspect of this embodiment, the composition is a pharmaceutical composition and the API or therapeutic agent is an anti-diabetic agent. In a further embodiment, the anti-diabetic agent is an antihyperlipidemic agent. In a further embodiment, the antihyperlipidemic agent is selected from statins, which are HMG CoA enzyme inhibitors, cholesterol absorption inhibitors, and cholesterol esterase transfer protein (CETP) inhibitors, and pharmaceutically acceptable salts and prodrugs thereof.

In one embodiment, the pharmaceutical composition comprises an antihyperlipidemic agent, preferably a statin, in physical admixture with two compounds of Formula III selected from the following:
calcium bis-lysinate bis-EPA and calcium bis-lysinate bis-DHA,
magnesium bis-lysinate bis-EPA and magnesium bis-lysinate bis-DHA,
magnesium bis-lysinate bis-EPA and magnesium bis-lysinate mono-EPA mono-DHA (also referred to as magnesium bis-lysinate bis EPA/DHA),
zinc bis-lysinate bis-EPA and zinc bis-lysinate bis-DHA,
calcium bis-arginate bis-EPA and calcium bis-arginate bis-DHA,
magnesium bis-arginate bis-EPA and magnesium bis-arginate bis-DHA,
zinc bis-arginate bis-EPA and zinc bis-arginate bis-DHA,
calcium bis-lysinate bis-EPA and calcium bis-lysinate bis-DPA,
magnesium bis-lysinate bis-EPA and magnesium bis-lysinate bis-DPA,
zinc bis-lysinate bis-EPA and zinc bis-lysinate bis-DPA,
calcium bis-lysinate bis-DHA and calcium bis-lysinate bis-DPA,
magnesium bis-lysinate bis-DHA and magnesium bis-lysinate bis-DPA,
zinc bis-lysinate bis-DHA and zinc bis-lysinate bis-DPA, and
calcium bis-lysinate bis-EPA and calcium bis-lysinate mono-EPA mono-DHA (also referred to as calcium bis-lysinate bis EPA/DHA).

In one embodiment, the pharmaceutical composition comprises an antihyperlipidemic agent, preferably a statin, in physical admixture with two compounds of Formula III selected from (i) calcium bis-lysinate bis-EPA and calcium bis-lysinate bis-DHA, (ii) magnesium bis-lysinate bis-EPA and magnesium bis-lysinate bis-DHA, and (iii) zinc bis-lysinate bis-EPA and zinc bis-lysinate bis-DHA.

The pharmaceutical compositions of the invention contain therapeutically effective amounts of each of the compound or compounds of Formula III contained in the composition and a therapeutically effective amount of the additional API or therapeutic agent, if present, in a single dosage form.

In one embodiment, the antihyperlipidemic agent is selected from a statin, a cholesterol absorption inhibitor, a CETP inhibitor, and a pharmaceutically-acceptable salt or prodrug thereof. The pharmaceutically acceptable salt may be selected from the group consisting of a propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenyl acetate, phenylpropionate, phenylbutyrate, citrate, lactate, p-hydroxybutyrate, glycolate, tartrate, methanesulfonate, propanesulfonates, naphthalene-1-sulfonate, naphthalene-2-sulfonate, mandelate, hippurate, gluconate, and lactobionate salt.

In one embodiment, the antihyperlipidemic agent is a statin. In one embodiment, the statin is selected from the group consisting of atorvastatin, risuvostatin, simvastatin, pravastatin, and pharmaceutically acceptable salts or prodrugs thereof. In one embodiment, the statin is present in the dosage form an amount ranging from 5 mg to 100 mg. In one embodiment, the statin is pravastatin.

In one embodiment, the antihyperlipidemic agent is a cholesterol absorption inhibitor. In one embodiment, the cholesterol absorption inhibitor is ezetimibe, also known as Zetia.

In one embodiment, the antihyperlipidemic agent is a CETP inhibitor. In one embodiment, the CETP inhibitor is anacetrapib, or a hydrate, or solvate thereof.

An excipient or carrier present in a pharmaceutical composition described herein is a pharmaceutically acceptable carrier or excipient. The term "pharmaceutically acceptable" indicates approval by a regulatory agency of the Federal or a state government or listed in the U.S. Pharmacopeia or other generally recognized pharmacopeia such as the European Pharmacopeia, for use in animals, and more particularly in humans. In the context of the pharmaceutical compositions of the invention, a "carrier" refers to, for example, a solvent, a diluent, or vehicle with which the ionic salt of the invention is formulated for delivery. Examples of pharmaceutically acceptable carriers for use in the compositions of the invention include, without limitation, sterile aqueous and non-aqueous liquids, water, buffered saline, ethanol, polyols (for example, glycerol, propylene glycol, liquid polyethylene glycol and the like), and oils, for liquid dosage forms; or carbohydrates (e.g., glucose, lactose, sucrose or dextran) for solid dosage forms.

The term "excipient" refers to an additive that serves some purpose in the composition other than a carrier, for example as a stabilizer, taste masking agent (e.g., a sweetener), solubilizing agent, or suspending agent. Often, a carrier will serve a dual purpose as a simple carrier or diluent and an excipient. Examples of pharmaceutically acceptable excipients may thus include carriers. Non-limiting examples of excipients for use in the compositions of the invention include sterile liquids, water, buffered saline, ethanol, polyols (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, and suitable mixtures thereof.

The compositions of the invention may be formulated in any suitable form and for any suitable intended route of administration. Typically, the dosage form is at least in part determined by the intended route of administration. In one embodiment, the dosage form is an oral dosage form. The oral dosage form may be in the form of a solid, such as a tablet, a capsule containing particulates, liquids, or powders, a lozenge (including liquid-filled), a gum, or a gel, or in the form of a liquid. In one embodiment, the pharmaceutical composition of the invention is formulated as a gel or cream suitable for topical administration. In one embodiment, the dosage form is a solid oral dosage form.

A pharmaceutical composition of the invention may be in the form of a unit dose. In one embodiment, the unit dose contains a therapeutically effective amount of a compound of Formula III. In one embodiment, the unit dose contains a therapeutically effective amount of a physical mixture of two or more compounds of Formula III. In one embodiment, the unit dose contains two compounds of Formula III in a ratio of from 1.25:1 to 4:1, or a ratio of 2:1, 3:1, or 5:4.

The compositions of the invention may be formulated as a nutraceutical additive or supplement. In this context, a nutraceutical additive or supplement of the invention may contain one or more compounds of Formula III. In one embodiment, the nutraceutical additive or supplement is in the form of a powder. In one embodiment, the nutraceutical additive or supplement is in the form of a liquid. In one embodiment, the nutraceutical additive or supplement is in the form of a mouth wash, a dentifrice, chewing gum, a candy, a tablet, a capsule, a mouth spray, or a film.

In one embodiment, the nutraceutical additive forms part of a food or drink product suitable for human consumption. There is no specific limitation on the foods/drinks to which a nutraceutical additive of the invention can be incorporated. Examples of such foods/drinks include processed foods based on meat, poultry meat, fish/shellfish and the like; soup; seasonings including sweetener and the like; rice seasonings; instant foods; frozen foods; snacks; various types of functional foods such as supplements, nutritional drinks and the like; canned foods; dairy products; confectionery such as chewing gum, candy, gummy candy, chocolate, baked sweets and the like; ice cream; soft drinks such as tea, coffee, cocoa, fruit juice, sports drink, carbonated drink, vegetable drink and the like; liquors; soya milk; lactic acid bacteria beverages; and chlorophyll juice.

The amount of a compound of Formula III incorporated into the food or drink as a neutraceutical additive varies in accordance with the type of food or drink and the amount that one wishes to supplement a diet with one or more omega-3 fatty acids. In one embodiment, the nutraceutical additive is incorporated into the food or drink so as to provide an amount of the omega-3 fatty acid that is about 0.000001 to 20% by weight, based on total weight of the food or drink product, and more preferably in an amount of about 0.00001 to 10% by weight.

Methods of Use

The compounds of the invention may be formulated into compositions suitable as nutraceutical additives or food products for human or animal use. In one embodiment, the additives or food products are for veterinary use.

Alternatively, the compounds of the invention may be formulated into pharmaceutical compositions for human or animal use. Pharmaceutical compositions of the invention are useful in methods of treating various diseases and disorders that are responsive to treatment with omega-3 fatty acids and/or the non-omega-3 therapeutic agent included in certain embodiments of the invention. In this context, the term "treating" may refer to the amelioration or stabilization of one or more symptoms associated with the disease or disorder. The term "treating" may also encompass the management of a disease or disorder, referring to the beneficial effects that a subject derives from a therapy which does not result in a cure of the underlying disease or disorder. For example, lowering elevated plasma triglycerides can be considered an aspect of treating diabetes because it is a beneficial effect that does not result in a cure of the underlying defect of glucose metabolism. The compositions of the invention can also be used in the prevention of certain diseases, disorders, and conditions. In this context, the term "prevention" refers to preventing the recurrence, development, progression or onset of one or more symptoms of the disease, disorder, or condition.

In accordance with the methods of the invention, a therapeutically effective amount of a composition of the invention is administered to a subject, the therapeutically effective amount being the amount sufficient to achieve a desired therapeutic outcome, for example the amelioration or stabilization of one or more symptoms of the disease or disorder being treated, or in the context of prevention, the amount sufficient to achieve prevention of the recurrence, development, progression or onset of one or more symptoms of the disease, disorder, or condition.

A subject in the context of the present invention may refer to either a human or animal subject. Accordingly, the methods of the invention contemplate both medical and veterinary uses.

In one embodiment, the subject is a human subject. In one embodiment, the human is an adult human, a pediatric human, or a geriatric human, as those terms are understood by the medical practitioner.

In one embodiment, the subject is an animal. In one embodiment, the animal is selected from the group consisting of a rodent, a non-human primate, a bird, a dog, a cat, a sheep, a goat, a horse, and a cow.

In one embodiment, a therapeutically effective amount is the amount required to achieve an equivalent therapeutic effect compared to a standard therapy. An example of a standard therapy is an FDA-approved drug indicated for treating a particular disease or disorder. For example, Vascepa™ is an FDA-approved formulation of EPA, specifically an ethyl ester of EPA. Accordingly, in one aspect, the methods of the invention include administering to a subject a therapeutically effective amount of a compound as described herein which is effective to reduce plasma triglycerides in an adult human subject by at least about 1 mmol/L, or by at least about 2 mmol/L.

In certain embodiments, the methods of the invention include administration of a composition of the invention as the primary therapy. In other embodiments, the administration of a composition of the invention is an adjuvant therapy. In either case, the methods of the invention contemplate the administration of a composition of the invention in combination with one or more additional therapies for the treatment or prevention of a disease or disorder. The terms "therapy" and "therapies" refer to any method, protocol and/or agent that can be used in the prevention, treatment, management or amelioration of a disease or disorder, or one or more symptoms thereof.

In the context of combination therapies, a composition of the invention may be administered together with the antihyperlipidemic agent or anti-diabetic agent or separately from the antihyperlipidemic agent or anti-diabetic agent. Where delivery is together with the antihyperlipidemic agent or anti-diabetic agent, the composition of the invention may be delivered in the same dosage form as the antihyperlipidemic agent or anti-diabetic agent, or in a different dosage form.

Antihyperlipidemic agents that may be used in the compositions of the invention include statins, which are HMG CoA enzyme inhibitors, cholesterol absorption inhibitors, and cholesterol esterase transfer protein (CETP) inhibitors, and pharmaceutically acceptable salts and prodrug thereof.

In one embodiment, the antihyperlipidemic agent is selected from a statin, a cholesterol absorption inhibitor, a CETP inhibitor, and a pharmaceutically-acceptable salt or prodrug thereof. The pharmaceutically acceptable salt may be selected from the group consisting of a propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenyl acetate, phenylpropionate, phenylbutyrate, citrate, lactate, p-hydroxybutyrate, glycolate, tartrate, methanesulfonate, propanesulfonates, naphthalene-1-sulfonate, naphthalene-2-sulfonate, mandelate, hippurate, gluconate, and lactobionate salt.

In one embodiment, the antihyperlipidemic agent is a statin. In one embodiment, the statin is selected from the group consisting of atorvastatin, risuvostatin, simvastatin, pravastatin, and pharmaceutically acceptable salts or prodrugs thereof. In one embodiment, the statin is present in an amount ranging from 5 mg to 100 mg. In one embodiment, the statin is pravastatin.

In one embodiment, the antihyperlipidemic agent is a cholesterol absorption inhibitor. In one embodiment, the cholesterol absorption inhibitor is ezetimibe, also known as Zetia.

In one embodiment, the antihyperlipidemic agent is a CETP inhibitor. In one embodiment, the CETP inhibitor is anacetrapib, or a hydrate, or solvate thereof.

In one embodiment, a composition of the invention is used in a method for treating a metabolic disorder selected from the group consisting of abnormal glucose metabolism manifesting in diabetes or pre-diabetes, abnormal lipid metabolism manifesting as hypertriglyceridemia, i.e., elevated triglycerides, mixed dyslipidemia, fatty liver, and combined abnormal glucose and lipid metabolism manifesting in obesity.

In one embodiment, a composition of the invention is used in a method for treating a disease or disorder selected from diabetes, pre-diabetes, hypertriglyceridemia, dyslipidemia, fatty liver, and obesity, the method comprising administering a therapeutically effect amount of the composition to treat one or more symptoms of the disease or disorder.

In one aspect, the methods of treating a metabolic disorder comprise administering to a subject in need of treatment for the metabolic disorder a pharmaceutical composition comprising two compounds of Formula III in a single dosage form. In one aspect of this embodiment, A and B are the same in each compound but different between the two compounds. For example, the first compound of Formula III in the composition may contain bis-EPA (A and B are both EPA), bis-DHA, or bis-DPA and the second compound of Formula III in the composition may contain any of the foregoing, provided it is different from the fatty acid component of the first compound. In a further aspect, one or both of the first and second compounds of Formula III in the composition contains a different omega-3 fatty acid at A and B. For example, one or both of the first and second compounds of Formula III may contain bis-EPA/DHA, bis-EPA/DPA, or bis-DHA/DPA, provided the fatty acid component of the first compound is different from that of the second. In one aspect of this embodiment, the two compounds of Formula III are present in the composition in a defined weight ratio. In a further aspect the defined ratio is from 1.25:1 to 4:1, or a ratio of 2:1, 3:1, or 5:4.

In one embodiment, the composition comprising a physical mixture of two compounds of Formula III comprises a mixture selected from
calcium bis-lysinate bis-EPA and calcium bis-lysinate bis-DHA,
magnesium bis-lysinate bis-EPA and magnesium bis-lysinate bis-DHA,
magnesium bis-lysinate bis-EPA and magnesium bis-lysinate mono-EPA mono-DHA (also referred to as magnesium bis-lysinate bis EPA/DHA),
zinc bis-lysinate bis-EPA and zinc bis-lysinate bis-DHA,
calcium bis-arginate bis-EPA and calcium bis-arginate bis-DHA,
magnesium bis-arginate bis-EPA and magnesium bis-arginate bis-DHA,
zinc bis-arginate bis-EPA and zinc bis-arginate bis-DHA,
calcium bis-lysinate bis-EPA and calcium bis-lysinate bis-DPA,
magnesium bis-lysinate bis-EPA and magnesium bis-lysinate bis-DPA,
zinc bis-lysinate bis-EPA and zinc bis-lysinate bis-DPA,
calcium bis-lysinate bis-DHA and calcium bis-lysinate bis-DPA,
magnesium bis-lysinate bis-DHA and magnesium bis-lysinate bis-DPA,
zinc bis-lysinate bis-DHA and zinc bis-lysinate bis-DPA and
calcium bis-lysinate bis-EPA and calcium bis-lysinate mono-EPA mono-DHA (also referred to as calcium bis-lysinate bis EPA/DHA).

In one embodiment, the composition comprising a physical mixture of two compounds of Formula III comprises the a mixture selected from (i) calcium bis-lysinate bis-EPA and calcium bis-lysinate bis-DHA, (ii) magnesium bis-lysinate bis-EPA and magnesium bis-lysinate bis-DHA, and (iii) zinc bis-lysinate bis-EPA and zinc bis-lysinate bis-DHA.

In a further aspect of this embodiment, the pharmaceutical composition further comprises a second API or therapeutic agent in the same dosage form as the two compounds of Formula III. In one aspect, the dosage form is a solid oral dosage form. In a further aspect of this embodiment, the pharmaceutical composition comprises an API selected from an antihyperlipidemic agent. In a further aspect, the antihyperlipidemic agent is a statin. In accordance with this embodiment, the pharmaceutical composition contains an amount of the compounds of Formula III effective to lower serum triglycerides in the subject being treated for the metabolic disorder as well as an amount of the antihyperlipidemic agent effective to lower serum cholesterol levels in the subject. In one embodiment, the composition comprises a physical mixture of two compounds of Formula III selected from (i) calcium bis-lysinate bis-EPA and calcium bis-lysinate bis-DHA, (ii) magnesium bis-lysinate bis-EPA and magnesium bis-lysinate bis-DHA, and (iii) zinc bis-lysinate bis-EPA and zinc bis-lysinate bis-DHA, and an antihyperlipidemic agent, preferably a statin, in the same dosage form, preferable a solid oral dosage form.

In one embodiment, the invention provides a method of treating insulin resistance in a subject, the method comprising administering to the subject a composition of the invention effective to treat insulin resistance in the subject. In one embodiment, the composition is a composition of Formula III where A and B are both docosahexaenoic acid anion (DHA anion, formula V), $R_1$ and $R_2$ are both lysine residues, and the metal is selected from magnesium, calcium, and zinc. In one embodiment, the composition is a composition of Formula III where A and B are both docosahexaenoic acid anion (DHA anion, formula V), $R_1$ and $R_2$ are both lysine residues, and the metal is magnesium (Formula XI).

In one embodiment, a composition of the invention is used in a method for treating cardiovascular complications relating to atrial fibrillation, myocardial infarction, and congestive heart failure. In one embodiment, a composition of the invention is used in a method for treating a cardiovascular condition selected from the group consisting of atrial fibrillation, myocardial infarction, and congestive heart failure, the method comprising administering a therapeutically effect amount of the composition to treat one or more symptoms of the cardiovascular condition.

In one embodiment, the compositions of the invention are used in a method for treating an inflammatory disorder, the method comprising administering a therapeutically effect amount of the composition to treat one or more symptoms of the inflammatory disorder. In one embodiment, the inflammatory disorder is selected from the group consisting of arthritis, inflammatory bowel disease, familial adenamatous polyposis and psoriasis.

In one embodiment, the compositions of the invention are used in a method for treating a disease or disorder of the ocular system, the method comprising administering a therapeutically effect amount of the composition to treat one or more symptoms of the disease or disorder of the ocular system. In one embodiment, the disease or disorder of the ocular system is selected from the group consisting of inflammatory diseases of the eye, dry eye syndrome, macular edema and retinopathy. In one embodiment, the compositions of the invention are used in a method for promoting corneal wound healing.

In one embodiment, the compositions of the invention are used in a method for treating a psychiatric disorder, the method comprising administering a therapeutically effect amount of the composition to treat one or more symptoms of the psychiatric disorder. In one embodiment, the psychiatric disorder is selected from Alzheimer's disease and attention deficit hyperactivity disorder (ADHD).

In one embodiment, the compositions of the invention are used in a method for treating traumatic brain injury, the method comprising administering a therapeutically effective amount of the composition to treat one or more symptoms of traumatic brain injury.

In one embodiment, the compositions of the invention are used in a method for preventing cancer. In one embodiment, the cancer is colon cancer.

In one embodiment, the compositions of the invention are used in a method for treating epilepsy or epileptic syndrome. In an aspect of this embodiment, the method comprises administering a pharmaceutical composition to a subject in need of treatment for epilepsy or epileptic syndrome, the pharmaceutical composition comprising a composition of Formula III where A is either EPA anion or DHA anion, B is gabapentin, $R_1$ and $R_2$ are both lysine residues or both arginine residues, and the metal is selected from magnesium, calcium, and zinc. In another aspect, both A and B are gabapentin.

In one embodiment, the compositions of the invention are used in a method for treating or managing pain. The pain may be neuropathic pain or nociceptive pain. In one embodiment, the pain is neuropathic pain and the method comprises administering a pharmaceutical composition to a subject in need of treatment for neuropathic pain, the pharmaceutical composition comprising a composition of Formula III where A is either EPA anion or DHA anion, B is a NSAID, $R_1$ and $R_2$ are both lysine residues or both arginine residues, and the metal is selected from magnesium, calcium, and zinc. In another aspect, both A and B are NSAIDs. In another embodiment, the pain is nociceptive pain and the method comprises administering a pharmaceutical composition to a subject in need of treatment for neuropathic pain, the pharmaceutical composition comprising a composition of Formula III where A is either EPA anion or DHA anion, B is gabapentin, $R_1$ and $R_2$ are both lysine residues or both arginine residues, and the metal is selected from magnesium, calcium, and zinc. In another aspect, both A and B are gabapentin.

For administration to human patients, the total daily dose of the compounds of the invention is typically in the range 1 g to 12 g depending, of course, on the mode of administration. In one embodiment the total daily dose is in the range 1 g to 10 g, in another embodiment the total daily dose is in the range 4 g to 8 g and in yet another embodiment the total daily dose is in the range 1 g to 2 g. The total daily dose may be administered in single or divided doses.

These dosages are based on an average human subject having a weight of about 65 kg to 70 kg. The physician will readily be able to determine doses for subjects whose weight falls outside this range, such as infants and the elderly.

The invention is further described in the following examples, which do not limit the scope of the invention described in the claims.

EXAMPLES

| Structure | Name | Characterization |
|---|---|---|
| Example 1 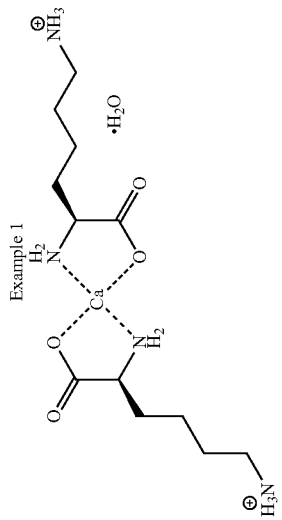 | Calcium bis-lysinate monohydrate (precursor) | Calcd for $C_{12}H_{26}CaN_4O_4 \cdot H_2O$: C, 41.36; H, 8.10; N, 16.08. Found: C, 41.36; H, 7.95; N, 15.93. $^1$H NMR (D$_2$O): δ 3.06 (t, 2H, J = 7 Hz); 2.42 (t, 4H, J = 7 Hz); 1.35-1.50 (m, 4H); 1.20-1.30 (m, 4H); 1.10-1.20 (m, 4H) |
| Example 2 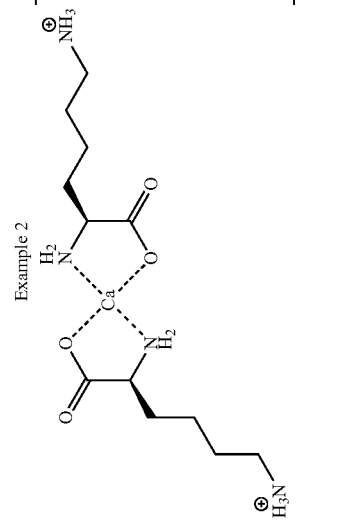 | Calcium bis-lysinate bis-EPA monohydrate | Calcd for $C_{52}H_{86}CaN_4O_8 \cdot H_2O$: C, 65.51; H, 9.30; N, 5.88. Found: C, 65.21; H, 9.06; N, 5.65. MP 138-141° C. $^1$H NMR (d4-AcOH): δ 5.25-5.50 (m, 20H); 4.01 (t, 2H, J = 6.5 Hz); 3.06 (t, 4H, J = 6.5 Hz); 2.75-2.90 (m, 16H); 2.36 (t, 4H, J = 6.5 Hz); 2.05-2.20 (m, 8H); 1.90-2.00 (m, 4H); 1.65-1.80 (m, 8H); 1.50-1.65 (m, 4H); 0.95 (t, 6H, J = 6.5 Hz). $^{13}$C NMR (d4-AcOH): δ 179.30, 174.08, 131.59, 128.71, 128.69, 128.24, 127.98, 127.97, 127.87, 127.68, 126.92, 54.33, 39.40, 32.87, 29.49, 26.18, 26.13, 25.22, 25.21, 25.11, 24.28, 21.37, 20.15, 13.48 |
| Formula VI 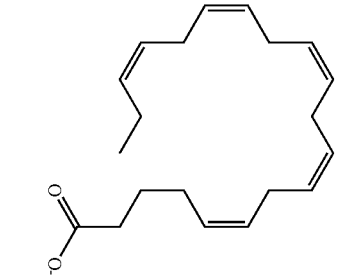 | | |
| Example 3 | Calcium | MP 141-143° C. $^1$H NMR |

-continued
| Structure | Name | Characterization |
|---|---|---|
| 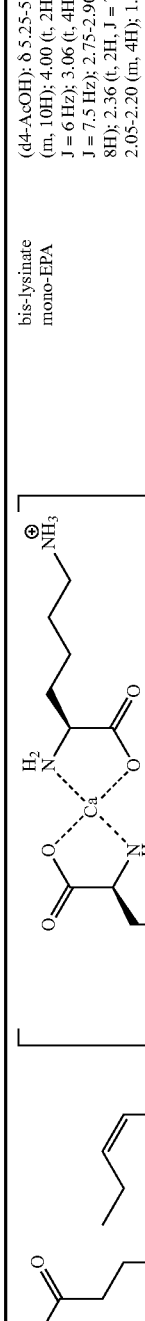 | bis-lysinate mono-EPA | (d4-AcOH): δ 5.25-5.45 (m, 10H); 4.00 (t, 2H, J = 6 Hz); 3.06 (t, 4H, J = 7.5 Hz); 2.75-2.90 (m, 8H); 2.36 (t, 2H, J = 7.5 Hz); 2.05-2.20 (m, 4H); 1.90-2.05 (m, 4H); 1.65-1.80 (m, 6H); 1.50-1.65 (m, 4H); 0.95 (t, 3H, J = 7.5 Hz). $^{13}$C NMR (d4-AcOH): δ 179.28, 174.14, 131.59, 128.71, 128.69, 128.24, 127.98, 127.96, 127.87, 127.68, 126.92, 54.34, 39.39, 32.88, 29.51, 26.20, 26.13, 25.22, 25.21, 25.11, 24.29, 21.39, 20.15, 13.48 |
| Formula VII | | |
| 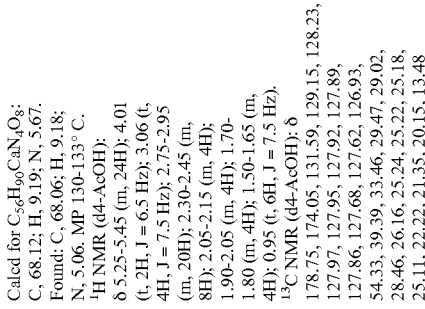<br>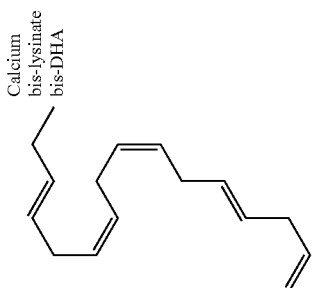 | Calcium bis-lysinate bis-DHA | Calcd for $C_{56}H_{90}CaN_4O_8$: C, 68.12; H, 9.19; N, 5.67. Found: C, 68.06; H, 9.18; N, 5.06. MP 130-133° C.<br>$^1$H NMR (d4-AcOH): δ 5.25-5.45 (m, 24H); 4.01 (t, 2H, J = 6.5 Hz); 3.06 (t, 4H, J = 7.5 Hz); 2.75-2.95 (m, 20H); 2.30-2.45 (m, 8H); 2.05-2.15 (m, 4H); 1.90-2.05 (m, 4H); 1.70-1.80 (m, 4H); 1.50-1.65 (m, 4H); 0.95 (t, 6H, J = 7.5 Hz). $^{13}$C NMR (d4-AcOH): δ 178.75, 174.05, 131.59, 129.15, 128.23, 127.97, 127.95, 127.92, 127.89, 127.86, 127.68, 127.62, 126.93, 54.33, 39.39, 33.46, 29.47, 29.02, 28.46, 26.16, 25.24, 25.22, 25.18, 25.11, 22.22, 21.35, 20.15, 13.48 |
| Formula VIII | | |
| Example 5 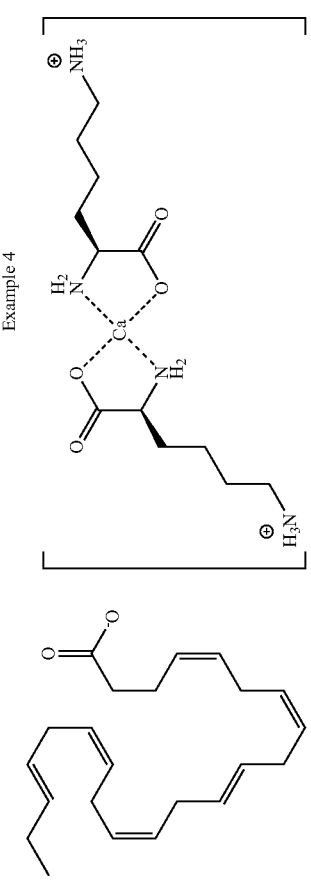 | Magnesium | $^1$H NMR (D$_4$-AcOH): δ |

| Structure | Name | Characterization |
|---|---|---|
| 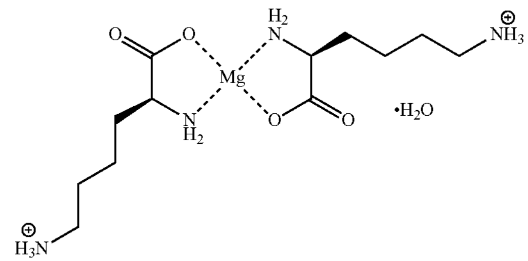 | bis-lysinate monohydrate (precursor) | 4.00 (t, 2H, J = 6 Hz); 3.06 (t, 4H, J = 7 Hz); 1.90-2.05 (m, 4H); 1.70-1.80 (m, 4H); 1.50-1.65 (m, 4H) |
| 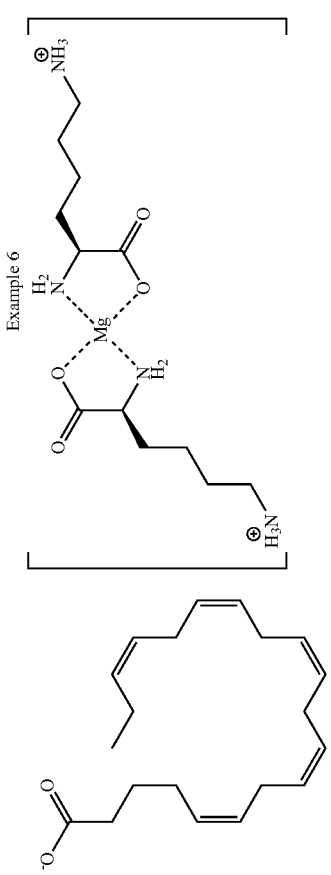 Example 6 Formula IX | Magnesium bis-lysinate bis-EPA Dihydrate | Calcd for $C_{52}H_{86}MgN_4O_8 \cdot 2H_2O$: C, 65.36; H, 9.49; N, 5.86. Found: C, 65.12; H, 9.49; N, 5.79. MP 153-155° C. $^1$H NMR (d4-AcOH): δ 5.25-5.45 (m, 20H); 4.01 (t, 2H, J = 6.5 Hz); 3.06 (t, 4H, J = 7.5 Hz); 2.80-2.90 (m, 16H); 2.37 (t, 4H, J = 7.5 Hz); 2.05-2.20 (m, 8H); 1.90-2.00 (m, 4H); 1.65-1.80 (m, 8H); 1.50-1.65 (m, 4H); 0.95 (t, 6H, J = 7.5 Hz). $^{13}$C NMR (d4-AcOH): δ 179.28, 173.98, 131.60, 128.71, 128.24, 127.99, 127.97, 127.88, 127.69, 126.93, 54.35, 39.40, 32.91, 29.53, 26.22, 26.15, 25.24, 25.22, 25.12, 24.30, 21.41, 20.17, 13.51 |
| Example 7 | Magnesium | MP 152-154° C. $^1$H NMR |

| Structure | Name | Characterization |
|---|---|---|
| (bis-lysinate mono-EPA structure with Mg) | bis-lysinate mono-EPA | (d4-AcOH): δ 5.25-5.45 (m, 10H); 3.99 (t, 2H, J = 6 Hz); 3.06 (t, 4H, J = 7.5 Hz); 2.75-2.90 (m, 8H); 2.36 (t, 2H, J = 7.5 Hz); 2.05-2.20 (m, 4H); 1.90-2.05 (m, 4H); 1.65-1.80 (m, 6H); 1.50-1.65 (m, 4H); 0.95 (t, 3H, J = 7.5 Hz). $^{13}$C NMR (d4-AcOH): δ 179.27, 173.97, 131.60, 128.71, 128.24, 127.99, 127.97, 127.88, 127.68, 126.93, 54.35, 39.40, 32.90, 29.53, 26.21, 26.14, 25.23, 25.21, 25.12, 24.30, 21.41, 20.16, 13.50 |
| Formula X<br>Example 8 | | |
| (Magnesium bis-lysinate bis-DHA dihydrate structure) ·2H$_2$O | Magnesium bis-lysinate bis-DHA Dihydrate | Calcd for $C_{56}H_{90}MgN_4O_8·2H_2O$: C, 66.75; H, 9.40; N, 5.56. Found: C, 67.05; H, 9.49; N, 5.30. MP 147-150° C.<br>$^1$H NMR (d4-AcOH): δ 5.25-5.45 (m, 24H); 4.01 (t, 2H, J = 6 Hz); 3.07 (t, 4H, J = 7.5 Hz); 2.75-2.95 (m, 20H); 2.35-2.45 (m, 8H); 2.05-2.15 (m, 4H); 1.90-2.05 (m, 4H); 1.70-1.80 (m, 4H); 1.50-1.65 (m, 4H); 0.95 (t, 6H, J = 7.5 Hz). $^{13}$C NMR (d4-AcOH): δ 178.76; 173.91, 131.59, 129.15, 128.24, 127.97, 127.95, 127.89, 127.86, 127.68, 127.62, 126.93, 54.33, 39.40, 33.46, 29.46, 26.16, 25.24, 25.23, 25.22, 25.18, 25.11, 22.21, 21.34, 20.16, 13.48 |
| Formula XI<br>Example 9 | Zinc bis- | $^1$H NMR (D$_4$-AcOH): δ |

| Structure | Name | Characterization |
|---|---|---|
| (Example 10 structure: zinc bis-lysinate complex) | lysinate (precursor) | 4.02 (m, 1H); 3.08 (m, 2H); 1.95-2.05 (m, 2H); 1.70-1.80 (m, 2H); 1.50-1.65 (m, 2H) |
| (Example 11 / Formula XII structure: Zinc bis-lysinate bis-EPA monohydrate) | Zinc bis-lysinate bis-EPA monohydrate | Calcd for $C_{52}H_{86}ZnN_4O_8 \cdot H_2O$: C, 63.82; H, 9.06; N, 5.72. Found: C, 63.67; H, 9.01; N, 5.76. MP 95-98° C. $^1$H NMR (d4-AcOH): δ 5.25-5.45 (m, 20H); 4.03 (m, 2H); 3.08 (t, 4H, J = 7.5 Hz); 2.80-2.90 (m, 16H); 2.36 (t, 4H, J = 7.5 Hz); 2.05-2.20 (m, 8H); 1.95-2.05 (m, 4H); 1.65-1.80 (m, 8H); 1.55-1.65 (m, 4H); 0.95 (t, 6H, J = 7.5 Hz) |
| | Magnesium | $^1$H NMR (d4-AcOH): δ 5.25- |

-continued
| Structure | Name | Characterization |
|---|---|---|
| 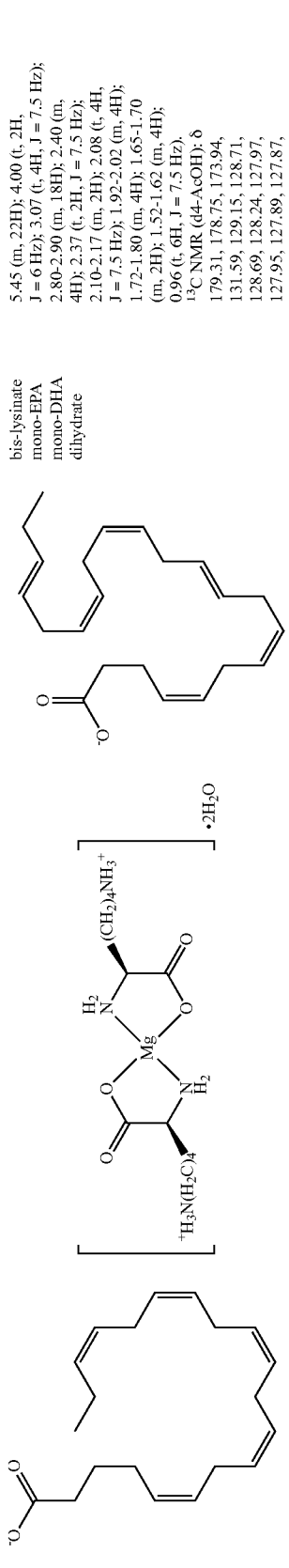 | bis-lysinate mono-EPA mono-DHA dihydrate | 5.45 (m, 22H); 4.00 (t, 2H, J = 6 Hz); 3.07 (t, 4H, J = 7.5 Hz); 2.80-2.90 (m, 18H); 2.40 (m, 4H); 2.37 (t, 2H, J = 7.5 Hz); 2.10-2.17 (m, 2H); 2.08 (t, 4H, J = 7.5 Hz); 1.92-2.02 (m, 4H); 1.72-1.80 (m, 4H); 1.65-1.70 (m, 2H); 1.52-1.62 (m, 4H); 0.96 (t, 6H, J = 7.5 Hz). $^{13}$C NMR (d4-AcOH): δ 179.31, 178.75, 173.94, 131.59, 129.15, 128.71, 128.69, 128.24, 127.97, 127.95, 127.89, 127.87, 127.68, 127.63, 126.92, 54.33, 39.39, 33.47, 32.88, 29.48, 26.18, 26.13, 25.24, 25.22, 25.18, 25.11, 24.28, 22.22, 22.05, 21.36, 20.16, 13.49. LCMS (m-1): lysine (145.9, 100%); EPA (301.8, 100%); DHA (327.8, 100%). |

1. Calcium Lysinate Salts

Calcium Bis-Lysinate Monohydrate

A solution of L-lysine (14.62 g, 100 mmol) in water (HPLC grade, 100 mL) under nitrogen was treated with calcium hydroxide (2.67 g). After a few minutes the solid had mostly dissolved, and an additional 1.48 g of calcium hydroxide was added, bringing the total to 4.15 g (56 mmol). The aqueous mixture was stirred at room temperature for 3 h. The turbid solution was filtered through Celite, the filter cake rinsed with HPLC grade water, and the filtrate concentrated in vacuo to afford 16.50 g (86%) of subject material as a colorless foam.

Calcd for $C_{12}H_{26}CaN_4O_4 \cdot H_2O$: C, 41.36; H, 8.10; N, 16.08. Found: C, 41.36; H, 7.95; N, 15.93. $^1H$ NMR ($D_2O$): δ 3.06 (t, 2H, J=7 Hz); 2.42 (t, 4H, J=7 Hz); 1.35-1.50 (m, 4H); 1.20-1.30 (m, 4H); 1.10-1.20 (m, 4H).

Calcium Bis-Lysinate Bis-EPA Monohydrate

A stirred solution of calcium bis-lysinate monohydrate (2.88 g, 7.5 mmol) in methanol (15 mL) was treated with a solution of EPA (4.84 g, 16 mmol) in methanol (15 mL) and stirred for 15 min, then diluted with acetonitrile (150 mL), stirred 30 min, and placed under refrigeration with cap for 24 h. The suspension was filtered and the waxy solid rinsed with acetonitrile and dried to afford 6.39 g (86%) of subject material as a pale orange solid.

Calcd for $C_{52}H_{86}CaN_4O_8 \cdot H_2O$: C, 65.51; H, 9.30; N, 5.88. Found: C, 65.21; H, 9.06; N, 5.65. MP 138-141° C. $^1H$ NMR (d4-AcOH): δ 5.25-5.50 (m, 20H); 4.01 (t, 2H, J=6.5 Hz); 3.06 (t, 4H, J=6.5 Hz); 2.75-2.90 (m, 16H); 2.36 (t, 4H, J=6.5 Hz); 2.05-2.20 (m, 8H); 1.90-2.00 (m, 4H); 1.65-1.80 (m, 8H); 1.50-1.65 (m, 4H); 0.95 (t, 6H, J=6.5 Hz). $^{13}C$ NMR (d4-AcOH): δ 179.30, 174.08, 131.59, 128.71, 128.69, 128.24, 127.98, 127.97, 127.87, 127.68, 126.92, 54.33, 39.40, 32.87, 29.49, 26.18, 26.13, 25.22, 25.21, 25.11, 24.28, 21.37, 20.15, 13.48.

Calcium Bis-Lysinate Mono-EPA

A stirred solution of calcium bis-lysinate monohydrate (1.92 g, 5.0 mmol) in methanol (10 mL) was treated with a solution of EPA (1.55 g, 5.125 mmol) in methanol (10 mL) and stirred for 15 min, then concentrated in vacuo to a pale yellow foam. The above foam was triturated from acetonitrile (20 mL) and dried in vacuo to afford 3.26 g (97%) of subject material as a pale yellow powder.

MP 141-143° C. $^1H$ NMR (d4-AcOH): δ 5.25-5.45 (m, 10H); 4.00 (t, 2H, J=6 Hz); 3.06 (t, 4H, J=7.5 Hz); 2.75-2.90 (m, 8H); 2.36 (t, 2H, J=7.5 Hz); 2.05-2.20 (m, 4H); 1.90-2.05 (m, 4H); 1.65-1.80 (m, 6H); 1.50-1.65 (m, 4H); 0.95 (t, 3H, J=7.5 Hz). $^{13}C$ NMR (d4-AcOH): δ 179.28, 174.14, 131.59, 128.71, 128.69, 128.24, 127.98, 127.96, 127.87, 127.68, 126.92, 54.34, 39.39, 32.88, 29.51, 26.20, 26.13, 25.22, 25.21, 25.11, 24.29, 21.39, 20.15, 13.48.

Calcium Bis-Lysinate Bis-DHA

A stirred solution of calcium bis-lysinate hydrate (1.533 g, 4.4 mmol) in methanol (15 mL) at 50° C. under nitrogen was treated with a solution of docosahexaenoic acid (DHA, 3.09 g, 9.4 mmol) in methanol (10 mL), allowed to cool to room temperature over 20 min, and partially concentrated in vacuo to remove most methanol. Acetonitrile (60 mL) was added, and the mixture stirred for 4 h, part of the time chilled. The pale yellow suspension was filtered and the amorphous solid rinsed with acetonitrile, collected and dried in vacuo to afford 4.26 g (98%) of subject material as a pale yellow solid.

Calcd for $C_{56}H_{90}CaN_4O_8$: C, 68.12; H, 9.19; N, 5.67. Found: C, 68.06; H, 9.18; N, 5.06. MP 130-133° C. $^1H$ NMR (d4-AcOH): δ 5.25-5.45 (m, 24H); 4.01 (t, 2H, J=6.5 Hz); 3.06 (t, 4H, J=7.5 Hz); 2.75-2.95 (m, 20H); 2.30-2.45 (m, 8H); 2.05-2.15 (m, 4H); 1.90-2.05 (m, 4H); 1.70-1.80 (m, 4H); 1.50-1.65 (m, 4H); 0.95 (t, 6H, J=7.5 Hz). $^{13}C$ NMR (d4-AcOH): δ 178.75, 174.05, 131.59, 129.15, 128.23, 127.97, 127.95, 127.92, 127.89, 127.86, 127.68, 127.62, 126.93, 54.33, 39.39, 33.46, 29.47, 29.02, 28.46, 26.16, 25.24, 25.22, 25.18, 25.11, 22.22, 21.35, 20.15, 13.48.

2. Magnesium Lysinate Salts

Magnesium Bis-Lysinate Monohydrate

A stirred mixture of magnesium hydroxide (1.75 g, 30 mmol) and L-lysine (8.77 g, 60 mmol) in reagent ethanol (30 mL) under nitrogen was heated to reflux for 6 h and cooled to room temperature. The thick suspension was filtered (slow) and rinsed with ethanol, collected, and dried in vacuo to afford 9.86 g (89%) of subject compound as a white solid.

$^1H$ NMR ($D_4$-AcOH): δ 4.00 (t, 2H, J=6 Hz); 3.06 (t, 4H, J=7.5 Hz); 1.90-2.05 (m, 4H); 1.71-1.78 (m, 4H); 1.52-1.63 (m, 4H). Elemental Analysis Calcd: C, 39.09; H, 8.75; N, 15.20. Found: C, 39.42; H, 8.47; N, 14.96. EA hits for trihydrate $C_{12}H_{26}MgN_4O_4 \cdot 3H_2O$.

Magnesium Bis-Lysinate Bis-EPA Dihydrate

A warmed (50° C.) stirred suspension of magnesium bis-lysinate monohydrate (1.844 g, 5.0 mmol) in methanol (10 mL) under nitrogen was treated with a solution of EPA (3.63 g, 12 mmol) in methanol (10 mL) containing alpha-D-tocopherol (100 mg) dissolved in ethyl acetate (0.5 mL), stirred for 20 min, then the mixture was concentrated in vacuo and suspended in acetonitrile (50 mL). The suspension was stirred for 3 h, filtered, washed with acetonitrile, collected and dried in vacuo to afford 4.78 g (100%) of magnesium lysinate bis EPA as a white solid.

NMR ($d_4$-AcOH): δ 5.27-5.44 (m, 20H) 4.00 (t, 2H, J=6 Hz) 3.06 (t, 4H, J=7.5 Hz) 2.80-2.89 (m, 16H) 2.36 (t, 4H, J=7.5 Hz) 2.05-2.16 (m, 8H) 1.91-2.00 (m, 4H) 1.65-1.78 (m, 8H) 1.54-1.63 (m, 4H) 0.95 (t, 6H, J=7.5 Hz). Elemental Analysis from previous batch: Calcd: C, 65.36; H, 9.49; N, 5.86. Found: C, 65.12; H, 9.49; N. Passes as a dihydrate.

Magnesium Bis-Lysinate Mono-EPA

A warmed (50° C.) stirred suspension of magnesium bis-lysinate monohydrate (1.00 g, 3.0 mmol) in methanol (5 mL) under nitrogen was treated with a solution of EPA (0.94 g, 3.1 mmol) in methanol (10 mL) containing alpha-D-tocopherol (100 mg) dissolved in ethyl acetate (0.5 mL), and stirred for 20 min, then most of the methanol was removed in vacuo and replaced with acetonitrile (20 mL). The mixture was stirred for 3 h, filtered, washed with acetonitrile, collected and dried in vacuo to afford 1.855 g (100%) of subject material as a pale beige solid.

MP 152-154° C. $^1H$ NMR (d4-AcOH): δ 5.25-5.45 (m, 10H); 3.99 (t, 2H, J=6 Hz); 3.06 (t, 4H, J=7.5 Hz); 2.75-2.90 (m, 8H); 2.36 (t, 2H, J=7.5 Hz); 2.05-2.20 (m, 4H); 1.90-2.05 (m, 4H); 1.65-1.80 (m, 6H); 1.50-1.65 (m, 4H); 0.95 (t, 3H, J=7.5 Hz). $^{13}C$ NMR (d4-AcOH): δ 179.27, 173.97, 131.60, 128.71, 128.24, 127.99, 127.97, 127.88, 127.68, 126.93, 54.35, 39.40, 32.90, 29.53, 26.21, 26.14, 25.23, 25.21, 25.12, 24.30, 21.41, 20.16, 13.50.

Magnesium Bis-Lysinate Bis-DHA Dihydrate

A warmed (50° C.) stirred suspension of magnesium bis-lysinate monohydrate (1.663 g, 5.0 mmol) in methanol (10 mL) under nitrogen was treated with a solution of DHA (3.53 g, 10.75 mmol) in methanol (10 mL) which had been combined with alpha-D-tocopherol (60 mg) in ethyl acetate (0.5 mL), and stirred for 20 min, then most of the methanol was removed in vacuo and replaced with acetonitrile (30 mL). The mixture was stirred for 3 h, filtered, washed with acetonitrile, collected and dried in vacuo to afford 4.85 g (96%) of subject material as a very pale beige solid.

Calcd for $C_{56}H_{90}MgN_4O_8 \cdot 2H_2O$: C, 66.75; H, 9.40; N, 5.56. Found: C, 67.05; H, 9.49; N, 5.30. MP 147-150° C. $^1H$ NMR (d4-AcOH): δ 5.25-5.45 (m, 24H); 4.01 (t, 2H, J=6 Hz);

3.07 (t, 4H, J=7.5 Hz); 2.75-2.95 (m, 20H); 2.35-2.45 (m, 8H); 2.05-2.15 (m, 4H); 1.90-2.05 (m, 4H); 1.70-1.80 (m, 4H); 1.50-1.65 (m, 4H); 0.95 (t, 6H, J=7.5 Hz). $^{13}$C NMR (d4-AcOH): δ 178.76; 173.91, 131.59, 129.15, 128.24, 127.97, 127.95, 127.89, 127.86, 127.68, 127.62, 126.93, 54.33, 39.40, 33.46, 29.46, 26.16, 25.24, 25.23, 25.22, 25.18, 25.11, 22.21, 21.34, 20.16, 13.48.

Magnesium Bis-Lysinate Mono-EPA Mono-DHA Dihydrate

A warmed (50° C.) stirred suspension of magnesium bis-lysinate trihydrate (1.844 g, 5.0 mmol) in methanol (25 mL) under nitrogen was treated with a solution of EPA (1.66 g, 5.5 mmol) and DHA (1.81, 5.5 mmol) in methanol (25 mL) which had been combined with alpha-D-tocopherol (100 mg) in ethyl acetate (1 mL), and stirred for 20 min, then the mixture was concentrated in vacuo and suspended in acetonitrile (75 mL). The mixture was stirred for 3 h, filtered, washed with acetonitrile, collected and dried in vacuo to afford 4.93 g (100%) of subject material as a pale beige solid.

MP 153-155° C. $^1$H NMR (d4-AcOH): δ 5.25-5.45 (m, 22H); 4.00 (t, 2H, J=6 Hz); 3.07 (t, 4H, J=7.5 Hz); 2.80-2.90 (m, 18H); 2.40 (m, 4H); 2.37 (t, 2H, J=7.5 Hz); 2.10-2.17 (m, 2H); 2.08 (t, 4H, J=7.5 Hz); 1.92-2.02 (m, 4H); 1.72-1.80 (m, 4H); 1.65-1.70 (m, 2H); 1.52-1.62 (m, 4H); 0.96 (t, 6H, J=7.5 Hz). $^{13}$C NMR (d4-AcOH): δ 179.31, 178.75, 173.94, 131.59, 129.15, 128.71, 128.69, 128.24, 127.97, 127.95, 127.89, 127.87, 127.68, 127.63, 126.92, 54.33, 39.39, 33.47, 32.88, 29.48, 26.18, 26.13, 25.24, 25.22, 25.18, 25.11, 24.28, 22.22, 22.05, 21.36, 20.16, 13.49. LCMS (m−1): lysine (145.9, 100%); EPA (301.8, 100%); DHA (327.8, 100%).

3. Zinc Lysinate Salts

Zinc Bis-Lysinate

A stirred solution of zinc chloride (6.82 g, 50 mmol) in water (100 mL) was treated with potassium hydroxide (5.8 g, 103.4 mmol) in water (30 mL), and the precipitate was stirred at room temperature for 20 min (pH~9.5). The suspension was filtered, the solid washed with water three times, with ethanol three times, collected and dried under high vacuum and 60° C. for 6 h to afford 4.79 g (96%) of zinc hydroxide as a white solid.

A stirred mixture of zinc hydroxide (4.48 g, 45 mmol) and L-lysine (13.45 g, 92 mmol) in ethanol (300 mL) was refluxed for 4 h (became very thick and required mechanical stirring). The above mixture was cooled to room temperature and filtered (slowly), collected, and dried in vacuo. The wet solid was triturated from acetonitrile and dried to afford 14.80 g (92%) of zinc bis-lysinate as a white powder.

$^1$H NMR (D$_4$-AcOH): δ 4.02 (m, 1H); 3.08 (m, 2H); 1.95-2.05 (m, 2H); 1.70-1.80 (m, 2H); 1.50-1.65 (m, 2H).

Zinc Bis-Lysinate Bis-EPA Monohydrate

A warmed (50° C.) stirred suspension of zinc bis-lysinate (1.78 g, 5.0 mmol) in methanol (15 mL) under nitrogen was treated with a solution of EPA (3.25 g, 10.75 mmol) in methanol (15 mL), at which point the solid dissolved. The solution was stirred for 20 min, then cooled to room temperature and concentrated in vacuo. The mixture was combined with acetonitrile (70 mL), and the suspension was stirred for 3 h, then filtered and the solid rinsed with acetonitrile, collected, and dried in vacuo to afford 4.48 g (92%) of subject compound as a pale tan solid.

Calcd for $C_{52}H_{86}ZnN_4O_8 \cdot H_2O$: C, 63.82; H, 9.06; N, 5.72. Found: C, 63.67; H, 9.01; N, 5.76. MP 95-98° C. $^1$H NMR (d4-AcOH): δ 5.25-5.45 (m, 20H); 4.03 (m, 2H); 3.08 (t, 4H, J=7.5 Hz); 2.80-2.90 (m, 16H); 2.36 (t, 4H, J=7.5 Hz); 2.05-2.20 (m, 8H); 1.95-2.05 (m, 4H); 1.65-1.80 (m, 8H); 1.55-1.65 (m, 4H); 0.95 (t, 6H, J=7.5 Hz).

Physical Stability Study

The compounds of the invention are remarkably stable compared to omega-3 polyunsaturated free fatty acids, which typically show evidence of oxidative degradation with hours of exposure to atmospheric oxygen. In contrast, as shown in FIG. 1, magnesium bis-lysinate bis-EPA was chemically stable for at least 60 days at room temperature exposed to air. The upper tracing in FIG. 1 is a proton NMR spectrum of magnesium bis-lysinate bis-EPA taken on the day the compound was synthesized. The lower tracing is the NMR taken 60-days later with the compound having been exposed to air at room temperature for the entire period. There is no evidence of oxidation or degradation by other mechanisms.

Bioavailability Study

The results of a single dose, oral pharmacokinetic study in rats for a compound of Formula III (designated TP-252, Mg-Lys$_2$-EPA$_2$) are shown in Table 1 below. One of the parameters shown in Table 1 is the area under the curve (AUC), which is the integral of a plot of concentration of drug in blood plasma against time. The AUC is proportional to the total amount of the active pharmaceutical agent (API) that reaches the blood circulation. In this example, the API (or analyte) is EPA. AUC and Cmax are given for the compound of Formula III, EPA free fatty acid (EPA FFA), and EPA ethyl ester (EPA EE). EPA ethyl ester is the FDA-approved form of EPA. These data demonstrate that TP-252 delivers significantly more EPA to the blood plasma than equivalent doses of either EPA free fatty acid or EPA ethyl ester.

TABLE 1

Baseline Adjusted, Molar Dose Equivalent Total EPA Plasma Levels (ug/mL)

|  | TP-252 | EPA EE | EPA FFA |
|---|---|---|---|
| Baseline and EPA Molar Dose Equivalent Adjusted |  |  |  |
| AUC$_{0-18\ hrs}$ | 132.9 | 56.4 | 85.5 |
| C$_{max}$ | 13.2 | 6.8 | 7.6 |
| Total Dose (mg/kg) | 40.0 | 40.0 | 40.0 |
| EPA Molar Dose (mg/kg) | 26.3 | 36.6 | 39.2 |
| EPA Molar Dose Equivalent Adjustment Factor | 1.49 | 1.07 | 1.00 |
| Predose Total EPA Plasma Concentration (Hour = 0) | 3.1 | 3.9 | 4.6 | a) The Baseline Adjusted, Molar Dose Equivalent plasma levels of Total EPA shown in Table 1 are calculated based on Baseline Adjusted Total EPA Plasma Concentration levels, multiplied by the EPA Molar Dose Adjustment Factors.
b) Baseline Adjusted, EPA Molar Dose Equivalent Cmax means the unadjusted Total EPA Cmax level minus the Total EPA predose level, multipled by the EPA Molar Dose Equivalent Adjustment Factors.
c) EPA Molar Dose (mg/kg) = Actual amount of EPA Free Fatty Acid delivered per kg of study subject.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A compound of Formula III having an amino acid component, which consists of two amino acids coordinated around a divalent metal cation, a metal component, which consists of a divalent metal cation, and a counter-ion component, which consists of one or two additional molecules, A and B, ionically bound to the amino acid component,

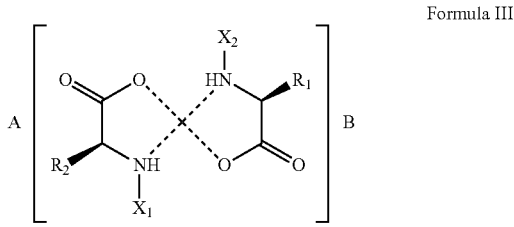

Formula III wherein $R_1$ and $R_2$ are the same or different and each is a side chain of an amino acid coordinated around X;

$X_1$ and $X_2$ are H;

X is selected from magnesium ($Mg^{2+}$), calcium ($Ca^{2+}$), or Zinc ($Zn^{2+}$) as the metal component;

A and B are each an omega-3 fatty acid, A and B are the same or different, and B is present or absent; and wherein B is present and A and B are independently selected from eicosapentaenoic acid (EPA), docosahexaenoic acid (DHA), and docosapentaenoic acid (DPA).

2. The compound of claim 1, wherein $R_1$ and $R_2$ are the same and selected from lysine or arginine amino acid side chains.

3. A composition comprising the compound of claim 2, and a carrier.

4. The composition of claim 3, wherein the composition comprises a mixture of two or more of the compounds in a single dosage form.

5. The composition of claim 4, wherein the composition is a pharmaceutical or nutriceutical composition and the carrier is acceptable for administration to humans.

6. The composition of claim 5, wherein the composition is a pharmaceutical composition.

7. The composition of claim 6, wherein the mixture comprises a first compound and a second compound.

8. The composition of claim 7, wherein A and B in each of the first and second compounds are independently selected from eicosapentaenoic acid (EPA), docosahexaenoic acid (DHA), and docosapentaenoic acid (DPA).

9. The composition of claim 8, wherein A and B are the same in each of the first second compounds, but different between the two compounds.

10. The composition of claim 9, wherein $R_1$ and $R_2$ are both lysine side chains.

11. The composition of claim 10, wherein X is magnesium.

12. The composition of claim 11, wherein A and B are both EPA in the first compound and A and B are both DHA in the second compound.

13. The composition of claim 12, wherein the first and second compounds are present in the composition in a weight ratio of from 1.25:1 to 4:1, or a ratio of 2:1, 3:1, or 5:4.

14. The composition of claim 13, further comprising an additional API or therapeutic agent in the same dosage form.

15. The composition of claim 14, wherein the API or therapeutic agent is an antihyperlipidemic agent.

16. The composition of claim 15, wherein the antihyperlipidemic agent is a statin, a cholesterol absorption inhibitor, a CETP inhibitor, or a pharmaceutically-acceptable salt or prodrug thereof.

17. The composition of claim 16, wherein the antihyperlipidemic agent is a statin.

18. The composition of claim 17, wherein the statin is selected from the group consisting of atorvastatin, risuvostatin, simvastatin, pravastatin, or a pharmaceutically acceptable salt or prodrug thereof.

19. The composition of claim 18, wherein the composition comprises an amount each of the compounds of Formula III effective to lower elevated serum triglycerides in a subject and an amount of the statin effective to lower serum cholesterol in the subject.

20. The composition of claim 19, wherein the subject is a human subject having severe hypertriglyceridemia.

21. The composition of claim 3 or 4, wherein the composition is a pharmaceutical composition and comprises an amount of a compound or compounds effective to treat insulin resistance, pre-diabetes, hypertriglyceridemia, dyslipidemia, fatty liver, or obesity in a subject, preferably a human subject.

22. The composition of claim 3 or 4, wherein the composition is a pharmaceutical composition and comprises an amount of a compound or compounds effective to treat a disease or disorder selected from the group consisting of arthritis, irritable bowel syndrome, atrial fibrillation, ophthalmic inflammation disorders, dry eye syndrome, traumatic brain injury, familial adenomatous polyposis, sporadic adenomatous polyposis, epilepsy, epileptic syndrome, Alzheimer's disease, and attention deficit hyperactivity disorder (ADHD).

23. The composition of claim 3 or 4, wherein the composition is a pharmaceutical composition and comprises an amount of a compound or compounds effective to treat or manage pain in a subject.

24. The composition of claim 23, wherein the additional therapeutic agent is gabapentin.

25. The composition of claim 23, wherein the additional therapeutic agent is a non-steroidal anti-inflammatory agent.

26. A package or kit comprising a unit dosage form of the composition of claim 3 or 4, at least one container for holding the unit dosage forms, and instructions for use.

27. A method of treating a disease or disorder in a subject, preferably a human subject, the method comprising administering to the subject an amount of the composition of claim 3 or 4 effective to treat the disease or disorder in the subject, the disease or disorder selected from the group consisting of hypertriglyceridemia, severe hypertriglyceridemia, pre-diabetes, fatty liver disease, obesity, arthritis, irritable bowel syndrome, atrial fibrillation, ophthalmic inflammation disorders, dry eye syndrome, traumatic brain injury, familial adenomatous polyposis, sporadic adenomatous polyposis, epilepsy, epileptic syndrome, Alzheimer's disease, pain of neuropathic or nociceptive origin, and attention deficit hyperactivity disorder (ADHD).

* * * * *